United States Patent [19]

Goodhue

[11] Patent Number: 4,499,184
[45] Date of Patent: Feb. 12, 1985

[54] ANALYSIS FOR TOTAL CHOLESTEROL USING LECITHIN:CHOLESTEROL ACYL TRANSFERASE (LCAT)

[75] Inventor: Charles T. Goodhue, Rochester, N.Y.

[73] Assignee: Eastman Kodak Company, Rochester, N.Y.

[21] Appl. No.: 383,849

[22] Filed: Jun. 1, 1982

[51] Int. Cl.³ .......................... C12Q 1/60; C12Q 1/48
[52] U.S. Cl. ........................................ 435/11; 435/15; 435/805; 436/71; 422/58
[58] Field of Search ....................... 435/11, 15, 18, 19, 435/25, 28, 805, 820; 422/58, 61, 68; 436/71

[56] References Cited

FOREIGN PATENT DOCUMENTS 1501561 2/1978 United Kingdom .

OTHER PUBLICATIONS

Glomset, *J. Lipid Res.*, 9:155–167, 1968.
MacIntyre and Buckley, *J. Bacteriol.*, 135: 402–407, 1978.
MacIntyre et al., *J. Bacteriol.*, 139: 132–136, 1979.

*Primary Examiner*—Blondel Hazel
*Attorney, Agent, or Firm*—J. Lanny Tucker

[57] ABSTRACT

Methods, compositions and elements for the analysis of total cholesterol in aqueous fluids containing cholesterol and cholesterol esters are disclosed. Cholesterol esters in the fluid samples are first converted to cholesterol by:

(a) contacting a sample of the fluid with sufficient amounts of lysolecithin and an enzyme exhibiting lecithin:cholesterol acyl transferase (LCAT) activity to convert substantially all the cholesterol esters to cholesterol in the sample, and (b) removing cholesterol from the aqueous fluid other than by conversion to cholesterol esters.

The total cholesterol is quantitatively determined by measuring the amount of the removed cholesterol. For example, the amount is measured gravimetrically or by converting the cholesterol to a detectable product.

28 Claims, No Drawings

ANALYSIS FOR TOTAL CHOLESTEROL USING LECITHIN:CHOLESTEROL ACYL TRANSFERASE (LCAT)

BACKGROUND OF THE INVENTION

1. Field of the Invention

The present invention relates to reagent compositions containing an enzyme exhibiting lecithin:cholesterol acyl transferase (LCAT) activity and to elements and methods for the use of such compositions in assaying for total cholesterol in liquids.

2. Discussion Relative to the Prior Art

Cholesterol is present in biological aqueous liquids such as serum or plasma, partially in free form and partially in the form of various cholesterol esters. Known quantitative analyses of total cholesterol (i.e., the sum of the cholesterol contributions from free and esterified cholesterol) include the use of corrosive chemicals to hydrolyze the cholesterol esters to free cholesterol followed by the analysis of the total free cholesterol in solution. In one conventional technique, the desired blood serum components are extracted with an organic solvent, the cholesterol esters are saponified with alcoholic KOH, and free cholesterol is isolated and assayed. In the assay, corrosive chemicals such as ferric perchlorate and sulfuric acid are employed.

More recently, enzymes have been used to convert cholesterol and cholesterol esters into detectable products. These processes usually entail the initial conversion of cholesterol esters to free cholesterol using cholesterol esterase enzymes, also referred to as cholesterol ester hydrolase enzymes. The use of cholesterol esterase enzymes in this manner is described in U.S. Pat. Nos. 3,869,349 issued Mar. 4, 1975, to Goodhue et al, and 3,983,005 issued Sept. 28, 1976, to Goodhue et al. These enzymes exhibit specific activity toward cholesterol esters to promote hydrolysis of the esters to cholesterol in aqueous medium. The terms "esterase" or "ester hydrolase" refer to an enzyme which catalyzes an hydrolysis reaction where water molecules react with the ester portion of the cholesterol ester molecule in the presence of the enzyme.

During or after esterase-promoted hydrolysis of the cholesterol ester, free cholesterol is converted to cholestenone and hydrogen peroxide in the presence of oxygen and cholesterol oxidase, and the hydrogen peroxide is detected by coupling with a dye precursor in the presence of peroxidase. These steps are well-known in the art.

Mammalian plasma is known to contain an enzyme characterized as lecithin:cholesterol acyl transferase (LCAT). It is postulated that this enzyme facilitates the transport of cholesterol from peripheral cells to the liver. The mechanism by which this occurs, as described by Glomset, J. A., *J.Lipid Res.*, 9:155-167, 1968, entails fatty acid acyl transfer from lecithin to cholesterol in the presence of LCAT as expressed by the following reaction:

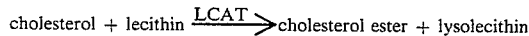

The propensity of LCAT to promote acyl transfer from lecithin to cholesterol has also been reported in British Pat. No. 1,501,561 published Feb. 15, 1978, as useful in the measurement of LCAT in serum. In this method, an assay medium composed of a surfactant and lecithin substrate solution is mixed with a test sample containing free cholesterol and serum level amounts of LCAT, and the mixture is incubated. LCAT activity is thereafter quantitated by colorimetrically detecting the disappearance of cholesterol in the mixture. In particular, after the assay mixture is incubated for 2-4 hours, it is treated with cholesterol oxidase, peroxidase and dye precursor to produce color in proportion to the amount of free cholesterol remaining after incubation. This procedure is based on the disappearance of cholesterol by conversion to cholesterol esters. Esters in the original sample are not converted to appreciable amounts, if any, of free cholesterol and their total quantity thus remains unknown. The patent does not teach nor suggest that LCAT can be employed to quantitate total cholesterol.

Bacterial enzymes exhibiting LCAT activity have been isolated from microorganisms. For example, it is reported that culture supernatants of *Aeromonas hydrophila* are enriched with a glycerophospholipid:cholesterol acyltransferase (GCAT), (MacIntyre, S., Buckley, J. T., *J. Bacteriol.*, 135: 402-407, 1978). The enzyme is said to deacylate human erythrocyte membrane glycerophospholipids—as LCAT does—resulting in the production of cholesterol esters. Other bacterial enzymes exhibiting LCAT-like activity include those isolated from the family Vibrionaceae and *Staphylococcus aureus* (MacIntyre, S., Trust, T. J., Buckley, J. T., *J. Bacteriol.*, 139: 132-136, 1979). The literature references pertaining to serum LCAT and to GCAT from microorganisms refer to the mechanism of these enzymes as applicable only to the conversion of cholesterol to cholesterol esters. That these enzymes can be employed in a reverse manner, i.e., to convert cholesterol esters to cholesterol, facilitating the quantitative determination of total cholesterol, is not reported nor suggested in the cited literature.

SUMMARY OF THE INVENTION

It has now been found that enzymes exhibiting lecithin:cholesterol acyl transferase (LCAT) activity are useful to quantitate total cholesterol in aqueous fluids containing cholesterol esters and cholesterol. This is achieved by stimulating the reversal of the reaction of cholesterol and lecithin in the presence of serum level amounts of LCAT to produce cholesterol esters, which is reported to occur in the prior art. In particular, cholesterol esters in a given sample of the aqueous fluid are converted to cholesterol by:

(a) contacting the sample with sufficient amounts of lysolecithin and an enzyme exhibiting LCAT activity to convert substantially all the cholesterol esters in the sample to cholesterol, and (b) removing cholesterol from the aqueous fluid other than by conversion to cholesterol esters.

Total cholesterol in the sample is quantitatively determined by measuring the amount of the removed cholesterol. The removal of cholesterol in step (b) is accomplished in a variety of ways such as by reaction of cholesterol with cholesterol oxidase to produce hydrogen peroxide. Measurement of total cholesterol is accomplished, for example, by converting the hydrogen peroxide to a colored dye by interaction with a peroxidase-dye coupled reagent.

In a preferred embodiment of the present invention, LCAT enzyme is obtained from a microbial source.

Preferably, the enzyme is obtained from the bacterial strain *Aeromonas hydrophila.*

In another preferred embodiment of this invention, lysolecithin is supplemented with or replaced by lecithin and an enzyme capable of catalyzing the hydrolysis of lecithin to lysolecithin. The lecithin is provided either as an additional reagent component or by its natural occurrence in certain liquid samples such as human serum.

In the described method, contact of a sample with sufficient amounts of LCAT and lysolecithin cooperates with the removal of cholesterol from the sample. If the latter step is absent, or if insufficient amounts of LCAT or lysolecithin are present, conversion of cholesterol esters to free cholesterol does not proceed to any appreciable extent. Accordingly, in the total cholesterol quantitative determination step, the results obtained would understate the true level of total cholesterol.

The method of quantitating total cholesterol with the defined LCAT is carried out in solution or within a clinical assay element in substantially dry (i.e., non-liquid-containing) form.

DESCRIPTION OF THE PREFERRED EMBODIMENTS

According to the present invention, an enzyme exhibiting LCAT activity and lysolecithin are employed with means for removing cholesterol to quantitate total cholesterol in a sample of an aqueous liquid. Although I do not intend to be bound by any theory or mechanism by which the present invention operates, it is believed that the LCAT enzyme and lysolecithin, when present in sufficiently large amounts, stimulate acyl transfer from cholesterol esters to the lysolecithin to form cholesterol and lecithin. The transfer is substantially complete (i.e., stoichiometric) if the LCAT promoted reaction is coupled with the removal of cholesterol from the sample fluid.

The method of the present invention for quantifying total cholesterol in an aqueous liquid entails:

(a) contacting a sample of the aqueous liquid with sufficient amounts of lysolecithin and an enzyme exhibiting LCAT activity to convert substantially all the cholesterol esters in the sample to cholesterol, (b) removing cholesterol from the sample other than by conversion to cholesterol esters, and (c) measuring the amount of the removed cholesterol.

This method for quantifying total cholesterol provides several advantages. It is an economically attractive alternative to known enzymatic approaches involving cholesterol esterases or cholesterol ester hydrolases. This method also provides a substantially complete conversion of cholesterol esters to cholesterol which yields precision and accuracy in the determination of total cholesterol, rapid results, and adaptability to solution assays and to dry-to-touch clinical assay elements.

The practice of the present invention includes the use of enzymes exhibiting lecithin:cholesterol acyl transferase (LCAT) activity in the presence of cholesterol esters and lysolecithin. LCAT enzymes differ from familiar cholesterol esterase or cholesterol ester hydrolase enzymes in several respects. Esterases or ester hydrolases mechanistically serve to hydrolyze cholesterol esters in aqueous medium wherein water acts as the acceptor molecule for the acyl group released during the reaction. LCAT, on the other hand, does not hydrolyze cholesterol esters. LCAT, as employed in the present invention, requires the presence of lysolecithin rather than water as an acyl-group acceptor. If lysolecithin is not present in a cholesterol ester aqueous solution containing LCAT, the conversion to cholesterol will not occur despite the presence of water.

Sources of LCAT enzyme include human plasma or serum. Serum LCAT is isolated, purified and characterized as disclosed by Glomset, J. A., *J. Lipid Res,* 9:155-167, 1968; Gustow, E., et al, *Scand. J. Clin. Lab. Invest.* 38, Suppl. 150, pp 1-5, 1978; K. Kitabatake et al, *Bioch. et Biophy, Acta,* 573, 145-154, 1979; and Fielding, C. J., *Scand. J. Clin. Lab. Invest.,* 33, Suppl. 137, 15-17, 1974.

A preferred LCAT is that obtained from culture supernatants of microorganisms and preferred microbial sources include microorganisms from the Vibrionaceae family, as well as from *Staphylococcus aureus* as disclosed by MacIntyre, S., Trust, T. J., Buckley, J. T., *J. Bacteriol.,* 139: 132-136, 1979, or *Phycomyces blakeleeanus* as disclosed by K. Bartlett, M. J. Keat and E. A. Mercer, *Photochemistry,* 13: 1107-1113, 1974. A most preferred LCAT is obtained from the culture supernatant of *Aeromonas hydrophila,* ATCC 9071, supplied by the American Type Culture Collection, Rockville, Md.

The amount of LCAT which, together with lysolecithin, is sufficient to convert substantially all cholesterol esters in a sample to cholesterol is dependent on a number of factors. Such amount is conveniently identified in terms of the concentration of the LCAT in the reagent-sample mixture, i.e., the total volume of sample plus reagent solution in a solution assay, or the sample volume which is estimated to reach the reagent zone in an assay conducted with a dry analytical element. On this basis, therefore, the LCAT concentration varies, for example, from about 3 to about 55 international units/liter with about 20 units/liter providing preferred results in serum samples. (The LCAT concentrations employed are in sharp contrast with normal serum LCAT concentrations of about $2 \times 10^{-5}$ Units/L).

In the cholesterol ester to cholesterol reaction step of the present invention, the presence of lysolecithin as an acyl-group acceptor is essential. Lysolecithin can be obtained commercially under the tradename L-α-lysophosphatidyl choline sold by Sigma Chemical Co., St. Louis, Mo. Alternatively, lysolecithin can be obtained by the enzymatic deacylation of lecithin in the presence of a hydrolyzing enzyme such as phospholipase A-2. In this regard, because lysolecithin is an expensive material, the LCAT reagent composition employed in accordance with the present invention can include lecithin in combination with an enzyme which catalyzes the hydrolysis of lecithin to lysolecithin. This combination produces lysolecithin in situ under assay conditions. Furthermore, because lecithin is generated as a by-product in the reaction of cholesterol esters and lysolecithin to produce cholesterol, the lecithin generated is hydrolyzed back to lysolecithin in the presence of the lecithin-hydrolyzing enzyme (see reaction scheme I below). A practical advantage, therefore, of employing the lecithin-hydrolyzing enzyme is to diminish the initial amount of lecithin required, there being sufficient amounts of lecithin formed during the course of reaction I:

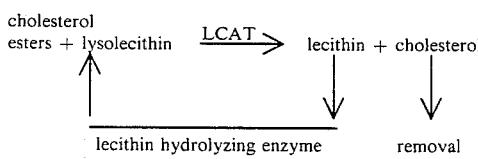

If desired, small amounts of lysolecithin are also employed with the lecithin and hydrolyzing enzyme to aid in the initiation of the LCAT-promoted reaction.

A preferred lecithin-hydrolyzing enzyme is phospholipase A-2 such as that recovered from the culture supernatant of *Aeromonas hydrophila*. Other examples of lecithin-hydrolyzing enzymes are lecithinase and phosphatide 2-acyl hydrolase. Because LCAT is also recoverable from the same supernatant, the enzyme preparation recovered from *Aeromonas hydrophila* is most preferred.

When human serum samples are assayed, moreover, the natural occurrence of lecithin in such samples is sufficient to initiate the in-situ formation of lysolecithin in the presence of a lecithin-hydrolyzing enzyme such as phospholipase A-2 recovered from the culture supernatant of *Aeromonas hydrophila*. Accordingly, the present invention is also practiced by (a) contacting an aqueous sample, such as human serum, containing cholesterol, cholesterol esters and lecithin, with sufficient amounts of an LCAT enzyme and a lecithin-hydrolyzing enzyme to convert substantially all the cholesterol esters in the sample to cholesterol, (b) removing cholesterol from the sample other than by conversion to cholesterol esters, and (c) measuring the amount of the removed cholesterol.

Preferably, the LCAT and lecithin-hydrolyzing enzyme are both derived from the microorganism *Aeromonas hydrophila*, the enzyme preparation so recovered containing both enzyme activities.

With the LCAT-stimulated conversion of cholesterol esters to cholesterol, there is employed the step of removing cholesterol from the sample undergoing assay for total cholesterol. As noted previously, stoichiometric (i.e., substantially complete) conversion of cholesterol esters is not effected in the absence of the cholesterol removal step. To this end, any means by which cholesterol can be removed is suitable so long as cholesterol is rendered unavailable for interacting with lecithin to produce cholesterol esters, the reverse of the desired reaction depicted in scheme I. Accordingly, one can physically remove cholesterol such as by complexation onto an appropriate substance. A typical complexing agent is digitonin, as described in *Research Disclosure*, Vol. 137, item 13739, published by Industrial Opportunities Ltd., Homewell, Havant, Hampshire, P09 1EF, United Kingdom. After complexation, the cholesterol is either decomplexed and measured as discussed below in connection with chemical removal of cholesterol, or determined gravimetrically.

Alternatively, and preferably, the cholesterol is removed by chemically changing it to a product other than a cholesterol ester. In a preferred embodiment of chemical removal, the cholesterol is enzymatically converted to a product with a second reagent composition composed of a second enzyme and reagents (e.g., buffers, activators, etc.) necessary to interact with the cholesterol to produce that product.

Cholesterol removal is commenced simultaneously or in sequence with contact between the aqueous liquid and LCAT and lysolecithin.

A preferred second enzyme employed in the cholesterol-removal step is cholesterol oxidase, which catalyzes decomposition of cholesterol in the presence of oxygen according to the following scheme:

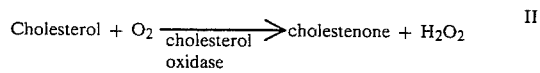

One of the products generated as a result of this reaction, $H_2O_2$, is employed to convert secondary reagents, in the presence of secondary enzymes, into a detectable product by any of a variety of well-known techniques such as by conversion of a color-forming substance to a colored species with color indicator systems disclosed in U.S. Pat. No. 3,983,005 issued Sept. 28, 1976, to C. T. Goodhue, et al.

According to a preferred embodiment of the present invention, cholesterol determination is achieved using an indicator composition which quantifies the level of hydrogen peroxide generated in the enzymatic oxidation of cholesterol. Indicator compositions for the detection of enzymatically generated hydrogen peroxide are well-known in the art, particularly as indicator compositions in the enzymatic detection of glucose and uric acid. U.S. Pat. Nos. 3,092,465 and 2,981,606 describe indicator compositions which are useful in the successful practice of the present invention. The hydrogen peroxide indicator compositions generally comprise a substance having peroxidative activity, preferably peroxidase, and an indicator material which undergoes a color formation or change in the presence of hydrogen peroxide and oxygen.

A peroxidase is an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase). Certain synthetic peroxidases, such as disclosed by Theorell and Maehly in *Acta Chem. Scand.*, Vol. 4, pages 422–434 (1950), are also useful. Also useful are such substances as hemin, methemoglobin, oxyhemoglobin, hemoglobin, hemochromogen, alkaline hematin, hemin derivatives, and certain other compounds which demonstrate peroxidative or peroxidase-like activity, namely, the ability to catalyze the oxidation of another substance by means of hydrogen peroxide and other peroxides.

Other substances which are not enzymes, but which demonstrate peroxidase-like activity, are iron sulfocyanate, iron tannate, ferrous ferrocyanide, chromic salts (such as potassium chromic sulfate) absorbed in silica gel, etc.

Alternatively, the indicator composition contains one or more substances which undergo no substantial color change upon oxidation in the presence of $H_2O_2$ and peroxidase, but which in their oxidized form react with a color-forming or color-changing substance to give visible quantitative evidence of chemical reaction. U.S. Pat. No. 2,981,606 in particular provides a detailed description of such color indicator compositions. The latter color-forming composition, i.e., one which produces color by virtue of an intermediate or color coupling reaction, is preferred in the practice of the present invention.

Color-forming substrates of peroxidase and peroxidase-like substances which produce a colored species in the presence of hydrogen peroxide and peroxidase which are used in the indicator of the present invention include the following substances (with a coupler where necessary):

1. Monoamines, such as aniline and its derivatives, ortho-toluidine, para-toluidine, etc;
2. Diamines, such as ortho-phenylenediamine, N,N'-dimethyl-para-phenylenediamine, N,N'-diethyl phenylenediamine, benzidine (which produces a blue or brown color), dianisidine (turns green or brown), etc.;
3. Phenols, such as phenol per se (producing a yellow color), thymol, ortho-, meta- and para-cresols (producing a green-yellow color, a pink color and a milky suspension, respectively), alpha-naphthol (producing a magenta color), beta-naphthol (producing a white precipitate), etc.;
4. Polyphenols, such as catechol, guaiacol (which forms an orange color), orcinol, pyrogallol (producing a reddish or yellow color), p,p-dihydroxydiphenyl and phloroglucinol;
5. Aromatic acids, such as salicyclic, pyrocatechuic and gallic acids;
6. Leuco dyes, such as leucomalachite green (to produce malachite green) and leucophenolphthalein (desirably employed in an alkaline medium);
7. Colored dyes, such as 2,6-dichlorophenolindophenol;
8. Biological substances, such as epinephrine, the flavones, tyrosine, dihydroxyphenylalanine (producing an orange-reddish color) and tryptophan;
9. Substances such as gum guaiac, guaiaconic acid, potassium, sodium and other water-soluble iodides, and bilirubin (producing a greenish color);
10. Such particular dyes as 2,2'-azinedi-(3-ethylbenzothiazoline-(6)-sulfonic acid) and 3,3'-diaminobenzidine; and
11. Mixtures of a sulfonyl hydrazone (or a precursor thereof) and a coupler, or a triarylimidazole, as disclosed in U.S. Pat. No. 4,089,747 issued May 16, 1978, to B. Bruschi.

The color indicator composition of the present invention preferably comprises:
(a) 4-methoxy-1-naphthol which undergoes self-coupling in its oxidized state, or
(b) a combination of 1,7-dihydroxynaphthalene and 4-aminoantipyrine (HCl).

In the latter composition, the oxidized concentrations of the components of the various color indicator compositions useful are dependent to a large extent upon the concentration of cholesterol in the sample, the sophistication of the detection apparatus, etc., and are readily determinable by the skilled artisan.

The present invention is readily adaptable to the solution, or "wet-chemistry" mode of assaying wherein the reagent components are provided in an aqueous reagent solution. Predetermined portions of the reagent solution are brought into contact with samples of aqueous liquid such as serum to be analyzed. In a preferred embodiment, however, the reagent components are incorporated into a dry element. Such elements remain essentially free from fluid until they are brought into contact with aqueous fluid to be analyzed. Suitable elements include conventional absorbant dip-and-read elements but most preferably are analytical elements comprising a spreading layer, one or more reagent layers and an optional support. Such analytical elements are described, for example, in U.S. Pat. Nos. 3,992,158 issued to Przybylowicz et al and 3,983,005 issued to C. T. Goodhue et al, both incorporated herein by reference.

In the following Examples, materials employed were as follows:

A lecithin:cholesterol acyltransferase (LCAT) was obtained from *Aeromonas hydrophila*, ATCC 9071, supplied by the American Type Culture Collection, Rockville, Md. The enzyme was purified according to the method described by MacIntyre, S., Buckley, J. T., *J. Bacteriol.*, 135:402–407, 1978, and partially characterized (molecular weight of 500,000).

Cultures of *Aeromonas hydrophila* were maintained on slants of a nutrient medium composed of 1% glucose, 1% yeast extract, 0.1% $K_2HPO_4$, 1.5% agar and 1% (v/v) salt solution "C" modified. Salt solution contains 0.1M $MgSO_4$, 0.01M $FeSO_4$, 0.01M NaCl, 0.01M $MnSO_4$, 0.4 mM $Na_2MoO_4$, 0.1 mM $ZnSO_4$ and 0.6 mM $CaCl_2$ dissolved in 0.1N HCl. Bacterial culture media ingredients were purchased from the Difco Company, Detroit, Mich. Agar ® was purchased from Oxoid Ltd., London, UK.

Cholesterol oxidase (COD) was obtained from *Streptomyces violascens* and from *Nocardia cholesterolicum*.

Peroxidase employed was horseradish type II, 152 purpurogallin units per mg solid. Other components include bovine serum albumin, L-α-lysophosphatidyl choline (lysolecithin from type I egg yolk); N-2-hydroxyethylpiperzine-N'-2-ethanesulfonic acid (HEPES) buffer; morpholinopropane sulfonic acid (MOPS) buffer; and tris[hydroxymethyl]aminomethane (TRIZMA). These components were obtained from the Sigma Chemical Company, St. Louis, Mo.

All remaining chemicals were supplied by Eastman Kodak Company, Rochester, N.Y.

PREPARATION OF A STANDARD CURVE FOR THE DETERMINATION OF TOTAL CHOLESTEROL (A) The time required to complete the reaction (endpoint), i.e., the conversion of esters to free cholesterol, was determined as follows:

A cholesterol linoleate stock solution (6.93 mM) was prepared in an aqueous solution composed of 15% Triton ® X-100 and served as the substrate for the enzyme lecithin-cholesterol acyltransferase (LCAT). Varying concentrations of substrate (0.35, 0.07, 1.1 and 1.4 mM) were prepared from this solution. A sample of each solution was added to a separate cuvette containing a reagent composition comprising 1.5% Triton ® X-100, 0.462 mM lysolecithin, $2 \times 10^{-2}$ units LCAT (cuvettes were preconditioned at 37° C. for 10 minutes before the addition of the enzyme) and 0.83 ml reagent buffer to obtain a final volume of 1.0 ml. The reagent buffer contained 1.4 mg peroxidase, 4 mg o-dianisidine (indicator), 12 units cholesterol oxidase, and 14 mg $CaCl_2$ (activator) prepared in 50 ml of 50 mM HEPES buffer, pH 7.0. A blank, which contained all components described above except the LCAT, was treated in the same manner as the substrate solutions. The change in absorbance at 430 nm was monitored for about 40 minutes in a spectrophotometer. The reaction was essentially complete in about 30 minutes, as indicated by no further increase in absorbance.

(B) A standard curve for the determination of total cholesterol was prepared as follows:

The total absorbance change of each sample (after 30 minutes) was monitored and plotted as a function of the cholesteryl linoleate concentration. Because these concentrations are stoichiometrically related to the cholesterol concentrations, the linear curve obtained by plotting absorbance change after 30 minutes versus known cholesterol ester concentrations served as the standard curve for the determination of total cholesterol.

EXAMPLES 1–14

Comparison of the Method of the Present Invention with the Reference Method—Solution Assay The endpoint assay for cholesteryl linoleate was applied to the determination of total cholesterol in serum samples. The Worthington Enzymatic Cholesterol kit (Worthington Biochemical Corp., Freehold, N.J.) served as the reference assay. This assay is a cholesterol oxidase reaction coupled with a peroxidase reaction. Fourteen cuvettes containing the components described in the reagent composition described in (A) above were preconditioned at 37° C. for 10 min. Serum samples were then added to obtain a final volume of 1.0 ml in each cuvette. The change in absorbance at 430 nm after 30 min was compared with values in the standard curve in (B) to determine the total cholesterol concentration (mM) in each sample. The results (converted from units of mM to mg) indicate excellent correlation between the method of the present invention and the reference method.

TABLE 1

Determination of Cholesterol Concentration in Serum Cholesterol (mg/cuvette)

| Example | LCAT-Coupled Assay Values | Reference Values |
| --- | --- | --- |
| 1 | .0291 | .0306 mg |
| 2 | .0282 | .0306 |
| 3 | .0363 | .0360 |
| 4 | .0366 | .0360 |
| 5 | .0394 | .0404 |
| 6 | .0402 | .0404 |
| 7 | .0557 | .0548 |
| 8 | .0549 | .0548 |
| 9 | .0402 | .0410 |
| 10 | .0220 | .0205 |
| 11 | .0201 | .0183 |
| 12 | .0394 | .0365 |
| 13 | .0296 | .0306 |
| 14 | .0293 | .0306 |

EXAMPLE 15

The Dry Analytical Element Employing the LCAT Reagent Composition of the Present Invention A dry multilayer analytical element having the following structure was prepared.

| Layer | Component | Concentration Per Meter$^2$ | |
| --- | --- | --- | --- |
| top reagent | LCAT (from *Aeromonas hydrophila*) | 538 | units |
| | cholesterol oxidase | 2,400 | units |
| | Triton X-100 ® | 8 | grams |
| | HEPES buffer to pH 7.0 | | |
| spreading | TiO$_2$ | 50 | grams |
| | cellulose acetate | 7 | grams |
| | Estane ® polyurethane | 1.8 | grams |
| subbing | poly(N—isopropylacrylamide) | 0.32 | gram |
| gel pad | gelatin | 5.4 | grams |
| | Alkanol X-C ® | 0.05 | gram |

-continued

| Layer | Component | Concentration Per Meter$^2$ | |
| --- | --- | --- | --- |
| bottom reagent | HEPES buffer to pH 7.0 gelatin | 5.4 | grams |
| | 4-isopropoxy-1-naphthol | 0.9 | gram |
| | 5,5-dimethyl-1,3-cyclohexandione | 0.21 | gram |
| | bis(vinylsulfonyl)methyl ether | 0.32 | gram |
| | poly(n-butyl methacrylate-co-styrene-co-2-acrylamido-2-methyl-propane sulfonic acid (50:40:10) | 5.2 | grams |
| | peroxidase | 16,000 | units |
| | HEPES buffer to pH 7.0 | | |
| support | 7-mil polyethylene terephthalate | | |

The foregoing element was employed to determine total cholesterol in serum samples containing cholesterol and cholesterol esters. The serum samples additionally contained lecithin (as a naturally occurring serum component) which was hydrolyzed to lysolecithin in situ by the lecithin-hydrolyzing enzyme phospholipase A-2 present in the LCAT (*Aeromonas hydrophila*) preparation. Results obtained correlated with a standard assay for total cholesterol.

Although the invention has been described in considerable detail with particular reference to certain preferred embodiments thereof, variations and modifications can be effected within the spirit and scope of the invention.

What is claimed is:

1. A method for determining total cholesterol in an aqueous fluid containing cholesterol esters and free cholesterol comprising:
   (a) contacting a sample of said fluid with sufficient amounts of lysolecithin and an enzyme exhibiting lecithin:cholesterol acyl transferase (LCAT) activity to convert substantially all the cholesterol esters in said sample to cholesterol,
   (b) removing cholesterol from said sample other than by conversion to cholesterol esters, and
   (c) measuring the amount of said removed cholesterol.

2. The method of claim 1 wherein the source of said enzyme is serum.

3. The method of claim 1 wherein the source of said enzyme is a microorganism.

4. The method of claim 3 wherein said microorganism is selected from the group consisting of *Staphylococcus aureus, Phycomyces blakesleeanus* and a member of the family Vibrionaceae.

5. The method of claim 3 wherein said microorganism is *Aeromonas hydrophila*.

6. A method for determining total cholesterol in an aqueous fluid containing cholesterol esters and free cholesterol comprising:
   (a) contacting a sample of said fluid with sufficient amounts of lysolecithin and an enzyme exhibiting lecithin:cholesterol acyl transferase (LCAT) activity to convert substantially all the cholesterol esters in said sample to cholesterol,
   (b) removing cholesterol from said sample by conversion to a detectable product other than a cholesterol ester, and
   (c) measuring the amount of said detectable product.

7. The method of claim 6 wherein said cholesterol is enzymatically reacted with oxygen to yield hydrogen peroxide, and hydrogen peroxide enzymatically converts a color-forming substance to a colored species as said detectable product.

8. The method of claim 6 wherein said cholesterol is enzymatically reacted with oxygen in the presence of cholesterol oxidase to yield hydrogen peroxide, and hydrogen peroxide converts a color-forming substance, in the presence of a material exhibiting peroxidative activity, to a colored species as said detectable product.

9. A method for determining total cholesterol in an aqueous fluid containing cholesterol esters and free cholesterol comprising:
(a) contacting a sample of said fluid with an enzyme exhibiting lecithin:cholesterol acyl transferase (LCAT) activity, lecithin, and a hydrolyzing enzyme capable of hydrolyzing lecithin to lysolecithin, each in sufficient amounts to convert substantially all the cholesterol esters in said sample to cholesterol,
(b) removing cholesterol from said sample other than by conversion to cholesterol esters, and
(c) measuring the amount of said removed cholesterol.

10. The method of claim 9 wherein said hydrolyzing enzyme is phospholipase A-2.

11. The method of claim 10 wherein said LCAT and phospholipase A-2 enzyme are derived from the microorganism *Aeromonas hydrophila* and said lecithin is provided by said aqueous fluid.

12. A composition for determining total cholesterol in an aqueous fluid containing free cholesterol and cholesterol esters comprising:
(a) a reagent composition comprising sufficient amounts of an enzyme exhibiting lecithin:cholesterol acyl transferase (LCAT) activity and lysolecithin to convert substantially all the cholesterol esters in a sample of said fluid to cholesterol,
(b) means for chemical removal of cholesterol from said sample other than by conversion to cholesterol esters, and
(c) means for chemical conversion of said removed cholesterol to a detectable product.

13. The composition of claim 12 wherein the source of said LCAT is a microorganism.

14. The composition of claim 13 wherein said microorganism is selected from the group consisting of *Staphylococcus aureus, Phycomyces blakesleeanus* and a member of the family Vibrionaceae.

15. The composition of claim 13 wherein said microorganism is *Aeromonas hydrophila*.

16. The composition of claim 12 wherein said means for chemical removal of cholesterol and said means for chemical conversion of said removed cholesterol is a second enzyme composition comprising cholesterol oxidase sufficient to convert said removed cholesterol to hydrogen peroxide, a color-forming substance sufficient to react with said hydrogen peroxide, and a material exhibiting peroxidative activity which catalyzes the reaction of said color-forming substance with hydrogen peroxide to produce a colored species as said detectable product.

17. A composition for determining total cholesterol in an aqueous fluid containing free cholesterol and cholesterol esters comprising:
(a) an enzyme exhibiting lecithin:cholesterol acyl transferase (LCAT) activity, lecithin, and a hydrolyzing enzyme capable of hydrolyzing lecithin to lysolecithin, each in sufficient amounts to convert substantially all the cholesterol esters in a sample of said fluid to cholesterol,
(b) means for chemical removal of cholesterol from said sample other than by conversion to cholesterol esters, and
(c) means for chemical conversion of said removed cholesterol to a detectable product.

18. The composition of claim 17 wherein said hydrolyzing enzyme is phospholipase A-2.

19. The composition of claim 17 wherein the source of said LCAT and phospholipase A-2 enzyme is the microorganism *Aeromonas hydrophila*.

20. The composition of claim 19 wherein said means for chemical removal of cholesterol and said means for chemical conversion of said removed cholesterol is a second enzyme composition comprising cholesterol oxidase sufficient to produce hydrogen peroxide from said removed cholesterol, a color-forming substance sufficient to react with said hydrogen peroxide, and a material exhibiting peroxidative activity which catalyzes the reaction of said color-forming substance with hydrogen peroxide to produce a colored species as said detectable product.

21. A composition for determining total cholesterol in an aqueous fluid containing cholesterol, cholesterol esters and lecithin comprising:
(a) sufficient amounts of an enzyme exhibiting lecithin:cholesterol acyl transferase (LCAT) activity and a hydrolyzing enzyme capable of hydrolyzing lecithin to lysolecithin, each in sufficient amounts to convert substantially all the cholesterol esters in a sample of said fluid to cholesterol,
(b) means for chemical removal of cholesterol from said sample other than by conversion to cholesterol esters, and
(c) means for chemical conversion of said removed cholesterol to a detectable product.

22. The composition of claim 21 wherein said LCAT and hydrolyzing enzyme are derived from the microorganism *Aeromonas hydrophila*.

23. A composition for converting cholesterol esters to cholesterol in an aqueous fluid containing cholesterol esters comprising:
(a) a reagent composition comprising sufficient amounts of an enzyme exhibiting lecithin:cholesterol acyl transferase (LCAT) activity and lysolecithin to convert substantially all the cholesterol esters in a sample of said fluid to cholesterol, and
(b) means for chemical removal of cholesterol from said sample other than by conversion to cholesterol esters.

24. A dry analytical element for determining total cholesterol in an aqueous fluid containing free cholesterol and cholesterol esters, said element comprising an absorbent layer, and a composition comprising:
(a) a reagent composition comprising sufficient amounts of an enzyme exhibiting lecithin:cholesterol acyl transferase (LCAT) activity and lysolecithin to convert substantially all the cholesterol esters in a sample of said fluid to cholesterol, and
(b) means for chemical removal of cholesterol from said sample other than by conversion to cholesterol esters.

25. A dry analytical element for determining total cholesterol in an aqueous fluid containing free cholesterol, cholesterol esters and lecithin, said element comprising an absorber layer, and a composition comprising:
(a) sufficient amounts of an enzyme exhibiting lecithin:cholesterol acyl transferase (LCAT) activity and a hydrolyzing enzyme capable of hydrolyzing lecithin to lysolecithin, each in sufficient amounts to convert substantially all the cholesterol esters in a sample of said fluid to cholesterol, (b) means for chemical removal of cholesterol from said sample other than by conversion to cholesterol esters, and (c) means for chemical conversion of said removed cholesterol to a detectable product.

26. An element as in claim 25 wherein said LCAT and hydrolyzing enzyme are derived from the microorganism *Aeromonas hydrophila*.

27. A dry analytical element for determining total cholesterol in an aqueous fluid containing free cholesterol and cholesterol esters, said element comprising an absorbent layer, and a composition comprising:

(a) a reagent composition comprising sufficient amounts of an enzyme exhibiting lecithin:cholesterol acyl transferase (LCAT) activity and lysolecithin to convert substantially all the cholesterol esters in a sample of said fluid to cholesterol, (b) means for chemical removal of cholesterol from said sample other than by conversion to cholesterol esters, and (c) means for chemical conversion of said removed cholesterol to a detectable product.

28. The dry analytical element of claim 27 wherein said absorbent layer is a spreading layer carried on a support.

* * * * *